United States Patent
Kaneda et al.

(10) Patent No.: US 10,351,862 B2
(45) Date of Patent: Jul. 16, 2019

(54) PROMOTER

(71) Applicant: Kao Corporation, Chuo-ku, Tokyo (JP)

(72) Inventors: Jitsuro Kaneda, Wakayama (JP);
Yuichi Tsuboi, Wakayama (JP);
Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/749,224

(22) PCT Filed: Jul. 27, 2016

(86) PCT No.: PCT/JP2016/071970
§ 371 (c)(1),
(2) Date: Jan. 31, 2018

(87) PCT Pub. No.: WO2017/022583
PCT Pub. Date: Feb. 9, 2017

(65) Prior Publication Data
US 2018/0223292 A1 Aug. 9, 2018

(30) Foreign Application Priority Data

Aug. 6, 2015 (JP) .................. 2015-155759
Oct. 9, 2015 (JP) .................. 2015-201180

(51) Int. Cl.
| | | |
|---|---|---|
| C12N 15/80 | (2006.01) | |
| C12P 1/02 | (2006.01) | |
| C12P 7/44 | (2006.01) | |
| C12N 9/24 | (2006.01) | |
| C12N 15/09 | (2006.01) | |

(52) U.S. Cl.
CPC ............... *C12N 15/80* (2013.01); *C12N 9/24* (2013.01); *C12N 15/09* (2013.01); *C12P 1/02* (2013.01); *C12P 7/44* (2013.01)

(58) Field of Classification Search
CPC .......... C12N 9/24; C12N 15/09; C12N 15/80; C12P 1/02; C12P 7/44; C12P 1/00
See application file for complete search history.

(56) References Cited

U.S. PATENT DOCUMENTS

| | | |
|---|---|---|
| 6,268,189 B1 | 7/2001 | Skory |
| 2002/0102636 A1 | 8/2002 | Gao et al. |
| 2006/0246560 A1 | 11/2006 | Fatland-Bloom et al. |
| 2010/0112651 A1 | 5/2010 | Fatland-Bloom et al. |

FOREIGN PATENT DOCUMENTS

| | | |
|---|---|---|
| JP | 2017-121184 A1 | 7/2017 |
| WO | WO 2001/072967 A2 | 10/2001 |
| WO | WO 2001/073083 A2 | 10/2001 |

OTHER PUBLICATIONS

Eder et al., Mutational analysis of the phoD promoter in Bacillus subtilis: implications for PhoP binding and promoter activation of Pho regulon promoters. J. Bacteriol., 1999, vol. 181(7): 2017-2025. (Year: 1999).*
Fischer et al., Characterization of the "promoter region" of the enolase-encoding gene enol from anaerobic fungus Neocallimastix frontalis: sequence and promoter analysis. Curr Genet., 1995, vol. 28: 80-86. (Year: 1995).*
Jeenes et al., 9 heterologous proetin production by filamentous fungi. Biotechnol. Genetic Eng. Rev., 1991, vol. 9:1: 327-367. (Year: 1991).*
Satola et al., Binding of Spo0A stimulates spoIIG promoter actiivity in Bacillus subtilis. J. Bacteriol., 1992, vol. 174(5): 1448-1453 (Year: 1992).*
International Search Report (ISR) for PCT/JP2016/071970; I.A. fd Jul. 27, 2016, dated Oct. 25, 2016 from the Japan Patent Office, Tokyo, Japan.
International Preliminary Report on Patentability (IPRP), Chapter I of the Patent Cooperation Treaty, including the Written Opinion for PCT/JP2016/071970; I.A. fd Jul. 27, 2016, dated Feb. 6, 2018, by the International Bureau of WIPO, Geneva, Switzerland.
Skory, CD, "Lactic acid production by *Rhizopus oryzae* transformants with modified lactate dehydrogenase activity," Appl Microbiol Biotechnol. Apr. 2004;64(2):237-42. Epub Nov. 18, 2003 Springer International, New York.
Mertens, JA et al., "Plasmids for expression of heterologous proteins in *Rhizopus oryzae*," Arch Microbiol. Jul. 2006;186(1):41-50. Epub Jun. 28, 2006 Springer-Verlag, New York.

* cited by examiner

*Primary Examiner* — Ganapathirama Raghu
(74) *Attorney, Agent, or Firm* — Sterne, Kessler, Goldstein & Fox P.L.L.C.

(57) ABSTRACT

Provided is a promoter suitable for the high expression of a gene of interest. A promoter consisting of a DNA selected from the group consisting of the following (a) to (d): (a) a DNA comprising the nucleotide sequence represented by any one of SEQ ID NOs: 1 to 3; (b) a DNA consisting of a nucleotide sequence having at least 70% identity to the nucleotide sequence represented by any one of SEQ ID NOs: 1 to 3 and having a promoter activity; (c) a DNA consisting of a nucleotide sequence wherein one or several of nucleotides are deleted, substituted or added in the nucleotide sequence represented by any one of SEQ ID NOS: 1 to 3 and having a promoter activity; and (d) a DNA which hybridizes with a DNA consisting of a nucleotide sequence complementary to the nucleotide sequence represented by any one of SEQ ID NOs: 1 to 3 under stringent conditions and which has a promoter activity.

21 Claims, No Drawings
Specification includes a Sequence Listing.

SEQUENCE LISTING

<160> NUMBER OF SEQ ID NOS: 26

<210> SEQ ID NO 1
<211> LENGTH: 1000
<212> TYPE: DNA
<213> ORGANISM: Rhizopus delemar

<400> SEQUENCE: 1

```
tagagggaaa aagagagaat tgaaatagga gaggatgagt caaaatatag tttacataaa      60
atttctcttt tttgtgttaa atataatcta atagcagggg ttttcttagt ttacgtttat     120
atcaaagtta tcaagcatac actttttat gattttcat actttaatcc cttttagtat      180
tctattgttt gaaggagag aaaaaacagc tgagggtacg gtgcacacga gatcttacga      240
taattttcct gcccaacagg aaagaagtaa ttgatcttga ttgacgctcg gagtttgcac     300
gttcggagtt tgcacttcac attgagttat actcttactt atttgaagg aagggacgag      360 aaaagatgta aatataataa taacagtagt aaatagtatg cgcatcaaga acagctacca    420
acaaaagaga gaaatatgag cttaataatg aacaatgtaa atggcagaat gaaattaat     480 tatcaaagcg gcatctttca gaccttccgt tacttccgat agagtttttt atgcaaagta    540
ataacaactg tatatataaa aaaaagaagg ttatcaagca aaagccacaa tgtcatatct   600
ggaataatca agagtaacta ttgaatgttg gtagccaaaa gaggcacgta atttatgac    660 gaaatatcac acaaaaagat tattttgaca attcatgaat aggacagaga tacaccctaa   720
acatgaaatg taagctatat ttaaacacct caagttaatt ttgaagcttc atttgtatta   780
ttgtaaccat ttagacaagc taaatccttt ttattattgt ccttattgat tttatccaga   840
ttaccgtatc taaagagcga tcaacagaaa aacggctgat tttagaccaa agtttcacaa   900
actacatttg catgaacgtc atatatatat aaaccttgac ttttcttttt ttttttttt    960 tttttttttc attatcaatt aatacaatta aataacaaaa                         1000
```

<210> SEQ ID NO 2
<211> LENGTH: 729
<212> TYPE: DNA
<213> ORGANISM: Rhizopus delemar

<400> SEQUENCE: 2

```
ggttactgaa actggtgtag aaattttaac atagaagcaa taaaacttac attcttccct     60
ctctttacat ctacgcatgt ttgccaagaa taaaatgcct catttcgggt atatcttttt    120
tagataggag ttgtaacttg taatattaag caatgtaacg gacttgtata ttttttaatca   180 aatacgtgtc gtgttttatt aaacgagcag aatcacttt ctatactgaa taaaagtaaa    240
aagaaccgaa tgcgttggta ataaattatt ttatcttttt ttttgtttt ttcacttgta     300 aaaaaccta aatgtttagg tttcatccgt tttcggctta gtaaaataag ctaaaagggc     360
ttgtggcgtt acacggctat taaactttac ataaagtaaa acatcatttg tcccttata    420 acaaaacgaa tgggaaaata accctccatc ttttaaaca aaatgagaaa ggtaacaata     480
acaaaaactg gaatgtgctt gggaaacttg aaaaaaagat aagcgcgtca ctcttgtttt    540 ctttttgtt tggttatgca taatattatt tgtacctcga aaaaaaatct tcggaatttg    600 tatttttat atatacggat gatagatgaa aaaggaaaa agctgatggg gcgtatgtat    660
ttgtcaaaaa agctataaaa gagcacaagt tttcacattt cgttttttt ttttcttcat    720 actctaacc                                                            729
```

```
<210> SEQ ID NO 3
<211> LENGTH: 1000
<212> TYPE: DNA
<213> ORGANISM: Rhizopus delemar

<400> SEQUENCE: 3
gatcatcaca agtattacac aatgttaatt ttaattaaat gtttgtcact gcaataaaat    60
ttgttaatga acaatgcaca tataaaaaat aaagtacaaa agaacataga tcaacacttt   120
gtataaaact cggtagaccc tttccttttc tttttttttt tttttttcct ttttctcttt   180 ttcttttttct tttttgtgt atatgcttct tttacaaaag aaaagaaaaa ggattgtatg   240
ctaatcgaac gcgtaaaaaa aaaggataaa ttattcggta ttctcaataa gacaactttt   300
ttttatttta gtgaatcaat tgaatgatgt cattttttact ttaagaaaaa tgagaaaaac   360
tattttcctt tctcttaaaa taagccaatg aagattaaca agatactaa tcttgaggat    420 caaagaagat atgagtcaat tgggttcccg gtccttttta tacatacttt tatataaaat   480
attctaaaaa caatttataa tctgctttga ctacagaaca acattcatt caattacaac    540 aagattcgct tttctctctt agaatcaagt tgttaagtaa ggatagctta cttttatgac   600 gaaccttttgt tatctaaatt tttgatgact gtaccttctg agttaattat atttgagtta  660
tttattacga gtatctatct ttaacactct gagggcttta ttttctcttt ttatttatac   720
aatgtgaaat aatgtataca aaaatcata caaaatacat atcacacgcg tgaacacaag    780
cgattactat atccttttgt gttgttgagc aaaatacaaa ttgtttatgc aaaaattcgt   840
tacactagat gccgattctc tccggtaaga gtttaagccc atctttcatc tacatctttt   900
ttttaaaaat ttttacgtac gcgtttcaat ataaagaga gagaaataac aattgctttt   960
tcctaacttt attttttgtga taattttta aaagcaaacc                       1000

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 4
cgagctcgaa ttatttaaat gaacagcaag ttaataatct agaggg             46

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
tatgaccatg attacgatga gaggcaaaat gaagcgtac                    39

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
atttaaataa ttcgagctcg gtacccgggg                              30
```

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cgtaatcatg gtcatagctg                                               20

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 8
tagagggaaa aagagagaat tgaaatagg                                     29

<210> SEQ ID NO 9
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 9
ttttgttatt taattgtatt aattgataat g                                  31

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
aattaaataa caaaatcatt ttaattacgc attttc                             36

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 11
catgattacg cggccgcgcc attataatgc actagtg                            37

<210> SEQ ID NO 12
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 12 ctcttttttcc ctctaatgag aggcaaaatg aagcgtac                          38

<210> SEQ ID NO 13
<211> LENGTH: 31
<212> TYPE: DNA
<213> ORGANISM: Artificial Sequence
<220> FEATURE:

```
<223> OTHER INFORMATION: Synthetic oligonucleotide

<400> SEQUENCE: 13
atttaaatgt aatcatggtc atagctgttt c                                31

<210> SEQ ID NO 14
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 14
aattaaataa caaaaatgtt acgtcctgta gaaacccca                         39

<210> SEQ ID NO 15
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 15
gcgtaattaa aatgatcatt gtttgcctcc ctgctgcgg                         39

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 16
ttttgttatt taattgtatt aattgataat g                                31

<210> SEQ ID NO 17
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 17
tcattttaat tacgcatttt catttactaa tttgttacat tttgataacg             50

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
cattttgcct ctcatggtta ctgaaactgg tgtag                             35

<210> SEQ ID NO 19
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 19
ctacaggacg taacatggtt agagtatgaa gaaaaaaaaa aaacg                  45
```

-continued

```
<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 20
atgttacgtc ctgtagaaac cccaac                                          26

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
atgagaggca aaatgaagcg tac                                             23

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22
cattttgcct ctcatgcaga cttcaacagt tggc                                 34

<210> SEQ ID NO 23
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 23
tacaggacgt aacatgtttt taaatttgtt ttgtagag                             38

<210> SEQ ID NO 24
<211> LENGTH: 1000
<212> TYPE: DNA
<213> ORGANISM: Rhizopus oryzae

<400> SEQUENCE: 24
attattatta gagggaaaaa aaagaaagag aattggttaa tgaaatagga gaggatgagt     60
caaaatataa tttacataaa atttctcttt ttgtattaaa tataatctaa tagcaggggt    120
tttcttagtt tacatttata acaaagttat caagtataca ctctttatg gttttcatg     180 ctttaatccc ttttagtatt ctattgtttg aaaggaaaga aaaacagct gagggtacgg    240 tgcacacgag atcttacgat aatttttcctg cccaacagga aaaagtaat tgatcttgat    300 tgacactcgg agtttgtatt tgacatagag ttctattctt acttatttga aggaaggggc    360
gagaaagatg taaatataat aatagcagta gtgaatagta tgtatatcaa gaacaactat    420
catcaaaaga aacaaatatg agcttaataa tgaacaatgt aaatggcaga atgaaattta    480
attatcaaag cggcatcttt cagactttcc gttacttccg atagagtttt ttatgcaaag    540
taataacaac tgtatataaa aaaaaagaa ggttatcaag caaaattcac aatgctatat     600
ctgaattaat caagagtaac tattgaatgt tggtatccaa aagaggcacg taattttatg    660
acgaaatatc acacaaaaag attattttga caattcataa ataggacaga gatacaccct    720
```

```
aaatatgaaa tgtaagctat atttaaacac cctgagttaa tcctgaagct tcatttgtat      780
tatcgtaagc atttagacaa gctgaatccc ttttattatt gtccgtattg attttattca      840
gattaccgta tctaaagagc gatcaacaga aaaacggctg attttagacc aaagtttcac      900
aaactacatt tgcatgaacg tcatatatat ataaaccttg acttttcatt ctttactttt      960 ttttttttc attatcaatt aatacaaata aataacaaaa                            1000

<210> SEQ ID NO 25
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 25
cattttgcct ctcatattat tattagaggg aaaaaaaaga aagagaattg g                51

<210> SEQ ID NO 26
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 26
tacaggacgt aacatttttg ttatttattt gtattaattg ataatg                      46
```

PROMOTER

FIELD OF THE INVENTION

The present invention relates to a novel promoter, an expression vector and a transformant comprising the promoter, and a method of producing a substance of interest using the transformant.

BACKGROUND OF THE INVENTION

In recent years, in addition to a chemical synthesis method, synthesis of a substance using an organism or an enzyme has been started to be conducted in an industrial level. Synthesis of a substance by an organism or an enzyme enables reduction of energy in synthesis compared to a chemical synthesis method, and also enables synthesis specialized in a specific structure of a compound having an optical isomer. Meanwhile, improvement of the productivity is one of important issues in industrial production of a useful substance by a microorganism. Conventionally, breeding of a production microbe through genetic approaches such as mutation have been conducted as an approach to improve the substance productivity of a microorganism. In particular, recently, more efficient microbiological production of a useful substance using a recombinant technique etc. has been drawing attention due to the development of microbial genetics and biotechnology.

So far, Rhizopus, a filamentous fungus, has been disclosed as a microorganism which can be used in the production of lactic acid (Patent Documents 1 to 3). However, in a fungus of Rhizopus, examples of the study on recombinant techniques etc. are few because genetic background was not clear, introduction of a molecular genetic approach was late, and isolation and maintenance of a monoclonal strain is expected to be difficult since a fungus of Rhizopus has multinucleated cells. Though a 1dhA promoter (Patent Literature 1, Non Patent Literature 1), a pgk1 promoter (Patent Literature 2, Non Patent Literature 2), a pgk2 promoter (Patent Literature 3), pdcA and amyA promoters (Non Patent Literature 2), tef and 18Sr RNA promoters (Patent Literature 4) etc. are reported as promoters necessary for the transcription of a gene in a fungus of Rhizopus, the intensity of expression of these promoters has not necessarily been examined comprehensively and promoters and microorganisms which achieve even higher productivity are required to reduce the production cost in industrial production.

[Patent Document 1] U.S. Pat. No. 6,268,189
[Patent Document 2] International Publication No. WO 2001/73083
[Patent Document 3] International Publication No. WO 2001/72967
[Patent Document 4] U.S. Unexamined Patent Application Publication No. 2010/112651
[Non Patent Document 1] Applied Microbiology and Biotechnology (2004) vol. 64:237-242
[Non Patent Document 2] Archives of Microbiology (2006) vol. 186:41-50

SUMMARY OF THE INVENTION

In one aspect, the present invention provides a promoter consisting of a DNA selected from the group consisting of the following (a) to (d):
(a) a DNA consisting of the nucleotide sequence represented by any one of SEQ ID NOs: 1 to 3;
(b) a DNA consisting of a nucleotide sequence having at least 70% identity to the nucleotide sequence represented by any one of SEQ ID NOs: 1 to 3 and having a promoter activity;
(c) a DNA consisting of a nucleotide sequence wherein one or several of nucleotides are deleted, substituted or added in the nucleotide sequence represented by any one of SEQ ID NOs: 1 to 3 and having a promoter activity; and
(d) a DNA which hybridizes with a DNA consisting of a nucleotide sequence complementary to the nucleotide sequence represented by any one of SEQ ID NOs: 1 to 3 under stringent conditions and which has a promoter activity.

In another aspect, the present invention provides an expression vector comprising the promoter.

In another aspect, the present invention provides a DNA fragment comprising a gene encoding a substance of interest or an enzyme involved in the synthesis of the substance and the promoter linked upstream of the gene.

In another aspect, the present invention provides a transformant comprising the expression vector or the DNA fragment.

In further one aspect, the present invention provides a method of producing a substance of interest, comprising: culturing the transformant; and collecting the substance of interest from a culture obtained in the culturing.

DETAILED DESCRIPTION OF THE INVENTION

In the specification, the identity of a nucleotide sequence refers to the maximal identity of a nucleotide sequence (%) obtained by introducing gaps as necessary into the two nucleotide sequences to be compared and aligning them. In the present invention, the sequence identity of a nucleotide sequence and an amino acid sequence is calculated by Lipman-Pearson Method (Science, 1985, 227: 1,435-1,441). Specifically, it is calculated by analyzing sequences with setting Unit size to compare (ktup) at 2 using a homology analysis (Search homology) program of a genetic information processing software, Genetyx-Win.

In the specification, "a promoter activity" refers to an activity which promotes the transcription of a DNA (a gene) into mRNAs. The promoter activity can be confirmed using an appropriate reporter gene. For instance, the promoter activity can be confirmed by linking a DNA encoding a detectable protein, i.e., a reporter gene, downstream of the promoter and measuring the production of the gene products of the reporter gene. Examples of the reporter gene include a β-galactosidase (LacZ) gene, a β-glucuronidase (GUS) gene, a luciferase gene, a β-lactamase gene and genes of fluorescent proteins such as a GFP (Green Fluorescent Protein) gene. Alternatively, the promoter activity can also be confirmed by measuring the expression level of mRNAs transcribed from the reporter gene using quantitative RT-PCR etc.

In the specification, the term "inherent" used for a function, a property and a trait of a microorganism is used to indicate that the function, the property and the trait are present in the wild type of the microorganism. In contrast, the term "exogenous" is used to indicate the function, the property and the trait which are not originally present in the microorganism, but are introduced from the outside. For instance, the gene introduced from the outside into a microorganism is an exogenous gene. The exogenous gene may be a gene derived from a microorganism allogeneic to the microorganism into which it is introduced or may be a gene derived from a xenogeneic organism (a xenogeneic gene).

In the specification, "upstream" and "downstream" with reference to a gene refer to the upstream and downstream of the transcriptional orientation of the gene. For instance, "a gene placed downstream of a promoter" means that the gene is present in the 3' side of the promoter in a DNA sense strand, and the upstream of a gene refers to the region of the 5' side of the gene in a DNA sense strand. In the specification, "operable linkage" between a promoter and a gene means that the promoter is linked so that the promoter may induce the transcription of the gene. The procedure of "operable linkage" between a promoter and a gene is well known to those skilled in the art.

The present invention relates to the provision of a novel promoter, and an expression vector and a transformant comprising the promoter, as well as a method of producing a substance of interest using the transformant.

The present inventors investigated a promoter derived from a filamentous fungus and found a novel promoter having a high transcriptional activity.

The promoter of the present invention has a high transcriptional activity and can significantly improve the transcript amount of the gene to be controlled. The promoter of the present invention can improve the efficiency of microbiological production of a substance of interest.

In one embodiment, the promoter of the present invention is a DNA consisting of the nucleotide sequence represented by any one of SEQ ID NOs: 1 to 3. In another embodiment, the promoter of the present invention encompasses a DNA consisting of a nucleotide sequence substantially same as the DNA comprising the nucleotide sequence represented by any one of SEQ ID NOs: 1 to 3 and having a promoter activity. Preferably, the promoter of the present invention has a 10% or more, preferably 15% or more, more preferably 50% or more, more preferably 70% or more, more preferably 80% or more and more preferably 90% or more promoter activity relative to the promoter activity of a DNA consisting of the nucleotide sequence represented by any one of SEQ ID NOs: 1 to 3.

Examples of the promoter of the present invention include a promoter consisting of a DNA defined by the following (a) to (d).
(a) a DNA consisting of the nucleotide sequence represented by any one of SEQ ID NOs: 1 to 3
(b) a DNA consisting of a nucleotide sequence having at least 70% identity to the nucleotide sequence represented by any one of SEQ ID NOs: 1 to 3 and having a promoter activity
(c) a DNA consisting of a nucleotide sequence wherein one or several of nucleotides are deleted, substituted or added in the nucleotide sequence represented by any one of SEQ ID NOs: 1 to 3 and having a promoter activity
(d) a DNA which hybridizes with a DNA consisting of a nucleotide sequence complementary to the nucleotide sequence represented by any one of SEQ ID NOs: 1 to 3 under stringent conditions and which has a promoter activity.

The DNAs consisting nucleotide sequences represented by SEQ ID NOs: 1 to 3 of the (a) are a promoter derived from *Rhizopus*. The DNA consisting of the nucleotide sequence represented by SEQ ID NO: 1 is a promoter of adh1, a gene encoding an alcohol dehydrogenase (ADH1) derived from *Rhizopus delemar*. The DNA consisting of the nucleotide sequence represented by SEQ ID NO: 2 is a promoter of cipC, a gene encoding a concanamycin responsive enzyme (CIPC) derived from *Rhizopus delemar*. The DNA consisting the nucleotide sequence represented by SEQ ID NO: 3 is a promoter of nmt1, a gene encoding a thiamine synthetase (NMT1) derived from *Rhizopus delemar*.

The nucleotide sequence having at least 70% identity to the nucleotide sequence represented by any one of SEQ ID NOs: 1 to 3 in the (b) refers to a nucleotide sequence having 70% or more, preferably 80% or more, more preferably 90% or more, further preferably 95% or more, further more preferably 98% or more, still preferably 99% or more identity to the nucleotide sequence represented by SEQ ID NO: 1, SEQ ID NO: 2 or SEQ ID NO: 3. Examples of the DNA of the (b) include an adh1 promoter DNA of *Rhizopus oryzae*, consisting of a nucleotide sequence represented by SEQ ID NO: 24 having 91% identity to the nucleotide sequence represented by SEQ ID NO: 1.

The nucleotide sequence in which one or several of nucleotides are deleted, substituted or added in the nucleotide sequence represented by any one of SEQ ID NOs: 1 to 3 in the (c) refers to a nucleotide sequence having deletion, substitution, or addition of one or several of nucleotides in the nucleotide sequence represented by SEQ ID NO: 1, SEQ ID NO: 2 or SEQ ID NO: 3. In the specification, "one or several of nucleotides" refers to 1 or more and 10 or less, preferably 1 or more and 5 or less, more preferably 1 or more and 3 or less and further preferably 1 or more and 2 or less nucleotides. The "deletion of a nucleotide" refers to lack or disappearance of a nucleotide in a sequence, and the "substitution of a nucleotide" means that a nucleotide in a sequence is replaced by another nucleotide, and the "addition of a nucleotide" means that a nucleotide is added to a sequence. "Addition" comprises addition of a nucleotide to one end or both ends of a sequence and insertion of another nucleotide between nucleotides in a sequence.

Examples of "stringent conditions" in the (d) include conditions of Southern hybridization described in Molecular Cloning-A LABORATORY MANUAL THIRD EDITION (Joseph Sambrook, David W. Russell., Cold Spring Harbor Laboratory Press, 2001), for instance, the condition in which DNAs are hybridized in a solution comprising 6×SSC (composition of 1×SSC: 0.15 M sodium chloride, 0.015 M sodium citrate, pH 7.0), 0.5% SDS, 5×Denhardt and 100 mg/mL herring sperm DNA with probes at constant temperature of 42° C. for 8 to 16 hours.

The method of obtaining the promoter of the present invention is not limited and the promoter can be obtained by a normal chemical synthesis method or genetic engineering approach. For instance, the promoter DNA of the present invention can be artificially synthesized based on the nucleotide sequences represented by SEQ ID NOs: 1 to 3. For instance, services from Invitrogen etc. can be used for the artificial synthesis of the DNA. Alternatively, the promoter sequences represented by SEQ ID NOs: 1 to 3 can be cloned from a microorganism such as *Rhizopus delemar*, for instance, according to the method described in Molecular Cloning-A LABORATORY MANUAL THIRD EDITION (Joseph Sambrook, David W. Russell, Cold Spring Harbor Laboratory Press, 2001).

The promoter DNA of the present invention may also be a DNA of the nucleotide sequences represented by SEQ ID NOs: 1 to 3 into which a mutation is introduced. Examples of the approach to introduce a mutation include, for instance, ultraviolet irradiation and site-specific mutation. Examples of the approach of the site-specific mutation include a method using Splicing overlap extension (SOE) PCR (Horton et al., Gene 77, 61-68, 1989), an ODA method (Hashimoto-Gotoh et al., Gene, 152, 271-276, 1995), and a Kunkel method (Kunkel, T. A., Proc. Natl. Acad. Sci. USA, 1985, 82, 488). Alternatively, commercially available kits to introduce a site-specific mutation such as Site-Directed Mutagenesis System Mutan-SuperExpress Km kit (TAKARA BIO INC.), Transformer™ Site-Directed Mutagenesis kit (Clontech Laboratories, Inc.), and KOD-Plus-Mutagenesis Kit (TOYOBO CO., LTD.) can be also used. The promoter DNA of the present invention can be obtained by selecting the DNA having the desired promoter activity from the mutated DNAs. For instance, the DNA having the promoter activity can be confirmed by operably linking a gene of interest downstream of the mutated DNAs and analyzing the expression level of the gene of interest.

A method for substitution, deletion or addition of nucleotides in a nucleotide sequence is described, for instance, in Dieffenbach et al. (Cold Spring Harbar Laboratory Press, New York, 581-621, 1995). A nucleotide sequence in which one or several nucleotides are substituted, deleted or added in the nucleotide sequence represented by any one of SEQ ID NOs: 1 to 3 can be obtained using the approach.

The promoter of the present invention has a function to control the expression of a gene placed downstream of the promoter. A DNA fragment having an expression control region excellent in a transcriptional activity can be obtained by using the promoter of the present invention. For instance, a DNA fragment comprising a gene of interest and the promoter of the present invention operably linked upstream of the gene can be constructed. The DNA fragment may comprise, in addition to the promoter of the present invention and a gene of interest, a cis-acting element which improves the transcriptional activity of the promoter. Further, the DNA fragment can be constructed so that the fragment has restriction enzyme recognition sequences on both ends. The promoter can be introduced to a vector using the restriction enzyme recognition sequences. That is to say, the promoter of the present invention can be introduced into a vector by cleaving a known vector by a restriction enzyme and adding thereto a DNA fragment comprising the promoter of the present invention and having a restriction enzyme cleavage sequence on its ends (a restriction enzyme method).

Alternatively, an expression vector which can improve the expression of a gene of interest in a transcriptional level can be obtained by integrating the promoter of the present invention into an expression vector which enables the expression of the gene of interest. The promoter of the present invention can be operably linked upstream of the DNA encoding the gene of interest in the expression vector. The expression vector having the promoter of the present invention may be introduced into chromosomes of a host cell or be retained extrachromosomally. Alternatively, a DNA fragment having the gene of interest and the promoter of the present invention operably linked upstream of the gene can be constructed and directory introduced into the genome of a host cell. In a filamentous fungus, the case is known that, by just introducing a linear DNA or a circular DNA without a replication origin into a cell, the DNA is retained in the cell (Skory et al., Current Genetics, 45, 302-310, 2004). Therefore, when the host cell is a filamentous fungus, the expression vector or the DNA fragment to be introduced need not necessarily have a replication origin.

The expression vector is not specifically limited as long as it is stably retained and can be grown within a host cell, and examples of the expression vector include, for instance, pUC18/19, pUC18/119, pBR322, pMW218/219, pPTR1/2 (TAKARA BIO INC.), pRI909/910 (TAKARA BIO INC.), pDJB2 (D. J. Ballance et al., Gene, 36, 321-331, 1985), pAB4-1 (van Hartingsveldt W et al., Mol Gen Genet, 206, 71-75, 1987), pLeu4 (M. I. G. Roncero et al., Gene, 84, 335-343, 1989), pPyr225 (C. D. Skory et al., Mol Genet Genomics, 268, 397-406, 2002) and pFG1 (Gruber, F. et al., Curr Genet, 18, 447-451, 1990).

The gene of interest placed downstream of the promoter of the present invention in the expression vector and the DNA fragment is not specifically limited. For instance, the gene of interest is a gene encoding a substance of interest or an enzyme involved in the synthesis of the substance. The gene of interest may be a heterologous gene encoding a heterologous expression product, or a gene encoding an expression product which the host cell inherently has, or a gene encoding any other proteins, peptides and nucleic acids etc. Examples of the substance encoded by the gene of interest include an enzyme, a hormone, a cytokine, other bioactive peptides, a transporter and a noncoding RNA. Examples of the enzyme include an oxidoreductase, a transferase, a hydrolase, a lyase, an isomerase, a ligase or a synthetase, a glycolytic enzyme, a lactic acid synthetase (LDH etc.) and an enzyme in the TCA cycle. Preferred examples of the gene of interest include a gene encoding an expression product which the host cell inherently has, for instance, a glycolytic enzyme, a lactic acid synthetase (LDH etc.), an enzyme in the TCA cycle, a transporter and a noncoding RNA etc., and more preferably include an enzyme involved in synthesis of an organic acid in a host cell such as a lactic acid synthetase, fumarate synthetase, a succinate synthetase, a malate synthetase, an α-ketoglutarate synthetase, an organic acid material uptake transporter, a glycolytic enzyme and an organic acid efflux transporter.

The promoter of the present invention does not compete with a promoter involved in the synthesis of an organic acid which is inherently present in a microorganism because the promoter of the present invention is a promoter for a gene of an enzyme which is not present in the organic acid metabolic pathway in the microorganism. Therefore, the promoter of the present invention can be suitably used as a promoter of a gene encoding the enzyme involved in the synthesis of the organic acid in microbiological organic acid production. Examples of the organic acid include preferably lactic acid, fumaric acid, succinic acid, malic acid and α-ketoglutaric acid.

The transformant of the present invention can be obtained by introducing an expression vector or a DNA fragment comprising the promoter of the present invention into a host cell using a typical transformation method, for instance, an electroporation method, a transforming method, a transfection method, a conjugation method, a protoplast method, a particle gun method and an *Agrobacterium* method etc.

The host cell into which the vector or the DNA fragment is introduced is not specifically limited as long as the promoter of the present invention functions as a promoter within the cell and usually includes a eukaryote, preferably a fungus, and more preferably a filamentous fungus. Examples of the preferred filamentous fungus include, for instance, a filamentous fungus of *Acremonium, Aspergillus, Aureobasidium, Bjerkandera, Ceriporiopsis, Chrysosporium, Copririus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes* and *Trichoderma*, and among these, a *Rhizopus* filamentous fungus such as *Rhizopus oryzae, Rhizopus arrhizus, Rhizopus chinensis, Rhizopus nigricans, Rhizopus tonkinensis, Rhizopus tritici* and

*Rhizopus delemar* is preferred, and *Rhizopus oryzae* and *Rhizopus delemar* are more preferred, and *Rhizopus delemar* is further preferred.

The transformant can be used to produce a substance of interest. For instance, a host cell transformed by an expression vector or a DNA fragment having a gene encoding a substance of interest or an enzyme involved in the synthesis of the substance and the promoter of the present invention operably linked upstream of the gene is cultured in an appropriate medium, and the gene is expressed under control of the promoter of the present invention, and the substance of interest is produced. The culture condition of the host cell is not specifically limited as long as the host cell can proliferate and the substance of interest can be produced. The substance of interest can be obtained by collecting the substance of interest from the culture after the completion of the culturing. Examples of the substance of interest include the substance encoded by the gene of interest and the product synthesized by the function of the substance, for instance, an organic acid produced by the enzyme involved in organic acid production. Examples of the organic acid include preferably lactic acid, fumaric acid, succinic acid, malic acid and α-ketoglutaric acid.

The production of a substance of interest using a filamentous fungus as a host can be conducted by culturing the filamentous fungus according to a typical culture method and collecting the substance of interest from the medium. For instance, the organic acid can be produced by culturing the spores or mycelia, or a mixture thereof of a filamentous fungus transformed by an expression vector having a gene encoding an enzyme involved in synthesis of the organic acid and the promoter of the present invention linked upstream of the gene in an appropriate medium at from 10 to 50° C., preferably from 25 to 35° C. for a few days. The number of days of culturing may be a period in which the organic acid of interest is produced enough. For instance, when the organic acid of interest is lactic acid, L-lactic acid or D-lactic acid is produced depending on the introduced gene by culturing them in the above-mentioned temperatures for from 1 to 168 hours, preferably from 2 to 72 hours, and particularly preferably from 4 to 24 hours. The medium is not specifically limited as long as a filamentous fungus grows soundly and can produce the organic acid of interest. For instance; a solid medium and liquid medium whose substrate is monosaccharide such as glucose and polysaccharide such as oligosaccharide and starch, and commercially available PDB medium (Becton, Dickinson and Company) and PDA medium (Becton, Dickinson and Company) etc. can be used.

To produce the organic acid more efficiently using the transformant whose host is a filamentous fungus, the organic acid can be produced according to the steps shown below. That is to say, the organic acid can be efficiently produced by preparing a suspension of the spores of the transformant (Step A), culturing the suspension in a culture solution to germinate the spores and prepare mycelia (Step B1), suitably, further growing the mycelia (Step B2), and then culturing the prepared mycelia to produce the organic acid (Step C).

<Step A; Preparation of the Suspension of the Spores>

The suspension of the spores can be prepared by inoculating the spores of a transformed filamentous fungus into a medium such as, for instance, an inorganic agar medium (example of the composition: 2% glucose, 0.1% ammonium sulfate, 0.06% potassium dihydrogenphosphate, 0.025% magnesium sulfate heptahydrate, 0.009% zinc sulfate heptahydrate and 1.5% agar, all concentrations are indicated in % (w/v)) and PDA medium, statically culturing them at from 10 to 40° C., preferably from 27 to 30° C. for 7 to 10 days to form spores, and suspending the spores in saline etc. The suspension of the spores may or may not comprise mycelia.

<Step B1: Preparation of Mycelia>

The suspension of the spores obtained above is inoculated into a culture solution and cultured, and the spores are germinated to obtain mycelia. The number of the spores of a filamentous fungus to be inoculated into the culture solution is from $1 \times 10^2$ to $1 \times 10^8$ spores/mL culture solution, preferably from $1 \times 10^2$ to $5 \times 10^4$ spores/mL culture solution, more preferably from $5 \times 10^2$ to $1 \times 10^4$ spores/mL culture solution, and further preferably from $1 \times 10^3$ to $1 \times 10^4$ spores/mL culture solution.

A commercially available medium, for instance, Potato dextrose medium (which hereinafter may be referred to as PDB medium. From, for instance, Becton, Dickinson and Company.), Luria-Bertani medium (which hereinafter may be referred to as LB medium. LB medium can be obtained from NIHON PHARMACEUTICAL CO., LTD. under the trade name "Daigo"), Nutrient Broth (which hereinafter may be referred to as NB medium. From, for instance, Becton, Dickinson and Company.), and Sabouraud medium (which hereinafter may be referred to as SB medium. From, for instance, OXOID.) etc. can be used as the culture solution for spore germination used in this step. Monosaccharides such as glucose and xylose, oligosaccharides such as sucrose, lactose and maltose, or polysaccharides such as starch as a carbon source; biological components such as glycerine and citric acid; ammonium sulfate, urea, amino acid etc. as a nitrogen source; and various salts of sodium, potassium, magnesium, zinc, iron, phosphoric acid, etc. as minerals can be appropriately added to the culture solution in terms of germination rate and growth of fungus bodies. The preferred concentration of monosaccharides, oligosaccharides, polysaccharides and glycerine is from 0.1 to 300 (w/v), and the preferred concentration of citric acid is from 0.01 to 10% (w/v), and the preferred concentration of ammonium sulfate, urea and amino acid is from 0.01 to 1% (w/v), and the preferred concentration of minerals is from 0.0001 to 0.50 (w/v).

In Step B1, the transformant filamentous fungus is cultured using the culture solution. Culture can be conducted according to a normal procedure. For instance, spores of the filamentous fungus are inoculated into a culture vessel containing the culture solution and cultured with stirring at preferably from 80 to 250 rpm, more preferably from 100 to 170 rpm under culture temperature control at from 25 to 42.5° C. for preferably from 24 to 120 hours, more preferably from 48 to 72 hours. The amount of the culture solution subjected to culture can be appropriately adjusted depending on the culture vessel, and, for instance, the amount may be about from 50 to 100 mL in the case of a 200 mL volume flask with baffles and about from 100 to 300 mL in the case of a 500 mL volume flask with baffles. The spores of the filamentous fungus are germinated and grown to mycelia by this culture.

<Step B2: Growth of Mycelia>

A step to grow mycelia obtained in Step B1 by further culturing them (Step B2) is preferably conducted in terms of the improvement of organic acid productivity. The culture solution for growth used in Step B2 is not specifically limited, and it may be an inorganic culture solution containing glucose usually used and examples of the solution include, for instance, a culture solution containing from 7.5 to 30% of glucose, from 0.001 to 2% of ammonium sulfate, from 0.001 to 0.6% of potassium dihydrogenphosphate, from 0.01 to 0.1% of magnesium sulfate heptahydrate, from 0.005 to 0.05% of zinc sulfate heptahydrate, and from 3.75 to 20% of calcium carbonate (all concentrations are indicated in % (w/v)) and, preferably, a culture solution containing 10% of glucose, 0.1% of ammonium sulfate, 0.06% of potassium dihydrogenphosphate, 0.025% of magnesium sulfate heptahydrate, 0.009% of zinc sulfate heptahydrate, and 5.0% of calcium carbonate (all concentrations are indicated in % (w/v)). The amount of the culture solution can be appropriately adjusted depending on the culture vessel, and for instance, the amount may be from 50 to 300 mL, preferably from 100 to 200 mL in the case of a 500 mL volume Erlenmeyer flask. The fungus bodies cultured in Step B1 are inoculated into this culture solution at from 1 to 20 g fungus bodies/100 mL medium, preferably from 3 to 10 g fungus bodies/100 mL medium in terms of wet weight and cultured with stirring at from 100 to 300 rpm, preferably from 170 to 230 rpm under culture temperature control at from 25 to 42.5° C. for 12 to 120 hours, preferably 24 to 72 hours.

<Step C: Production of Organic Acid>

The mycelia of the filamentous fungus obtained in the above procedures (B1 or B1 and B2) are cultured to make the fungus produce organic acids and then the produced organic acids can be collected.

The culture solution for the production of an organic acid used in Step (C) may be a culture solution containing a carbon source such as glucose, a nitrogen source such as ammonium sulfate and various metal salts in which organic acids can be produced. Examples of the culture solution used in Step (C) include, for instance, a culture solution containing from 7.5 to 30% of glucose, from 0.001 to 2% of ammonium sulfate, from 0.001 to 0.6% of potassium dihydrogenphosphate, from 0.01 to 0.1% of magnesium sulfate heptahydrate, from 0.005 to 0.05% of zinc sulfate heptahydrate and from 3.75 to 20% of calcium carbonate (all concentrations are indicated in % (w/v)), preferably, a culture solution containing 12.5% of glucose, 0.1% of ammonium sulfate, 0.06% of potassium dihydrogenphosphate, 0.025% of magnesium sulfate heptahydrate, 0.009% of zinc sulfate heptahydrate and 5.0% of calcium carbonate (all concentrations are indicated in % (w/v)).

The amount of the culture solution used in Step (C) can be appropriately adjusted depending on the culture vessel, and for instance, the amount may be about from 20 to 80 mL in the case of 200 mL volume Erlenmeyer flask and about from 50 to 200 mL in the case of 500 mL volume Erlenmeyer flask. The fungus bodies are inoculated into this culture solution at from 5 to 90 g fungus bodies/100 mL culture solution, preferably from 5 to 50 g fungus bodies/100 mL culture solution in terms of wet weight and cultured with stirring at from 100 to 300 rpm, preferably from 170 to 230 rpm under culture temperature control at from 25 to 45° C. for 2 to 72 hours, preferably from 4 to 36 hours.

Organic acids can be obtained by collecting the culture supernatant from the culture solution. The organic acids in the culture solution can be collected as organic acid salts and then the organic acids can be isolated or purified from the collected organic acid salts using decantation, membrane separation, centrifugation, electrodialysis, application of an ion exchange resin, distillation, salting-out or combinations thereof as necessary.

The following substances, production methods, use, or methods are further disclosed in the specification as exemplary embodiments of the present invention. However, the present invention is not limited to these embodiments.

<1> A promoter consisting of a DNA selected from the group consisting of the following (a) to (d):

(a) a DNA consisting of the nucleotide sequence represented by any one of SEQ ID NOs: 1 to 3;

(b) a DNA consisting of a nucleotide sequence having at least 70% identity to the nucleotide sequence represented by any one of SEQ ID NOs: 1 to 3 and having a promoter activity;

(c) a DNA consisting of a nucleotide sequence wherein one or several nucleotides are deleted, substituted or added in the nucleotide sequence represented by any one of SEQ ID NOs: 1 to 3 and having a promoter activity; and (d) a DNA which hybridizes with a DNA consisting of a nucleotide sequence complementary to the nucleotide sequence represented by any one of SEQ ID NOs: 1 to 3 under stringent conditions and which has a promoter activity.

<2> The promoter according to <1>, wherein the DNA shown in the (b) is a DNA consisting of a nucleotide sequence having preferably 80% or more, more preferably 90% or more, further preferably 95% or more, further preferably 98% or more and still preferably 99% or more identity to the nucleotide sequence represented by any one of SEQ ID NOs: 1 to 3.

<3> The promoter according to <1>, wherein the DNA shown in the (c) is a DNA consisting of a nucleotide sequence having deletion, substitution, or addition of preferably 1 or more and 10 or less, more preferably 1 or more and 5 or less, further preferably 1 or more and 3 or less, further more preferably 1 or more and 2 or less nucleotides in the nucleotide sequence represented by any one of SEQ ID NOs: 1 to 3.

<4> An expression vector comprising the promoter according to any one of <1> to <3>.

<5> The expression vector according to <4>, preferably comprising a gene encoding a substance of interest or an enzyme involved in synthesis of the substance and the promoter according to any one of <1> to <3> operably linked to the gene.

<6> The expression vector according to <4>, wherein the promoter is preferably linked upstream of the gene encoding a substance of interest or an enzyme involved in synthesis of the substance.

<7> The expression vector according to <5> or <6>, wherein the gene is preferably a gene encoding an enzyme involved in synthesis of an organic acid.

<8> A DNA fragment comprising a gene encoding a substance of interest or an enzyme involved in synthesis of the substance and the promoter according to any one of <1> to <3> linked upstream of the gene.

<9> The DNA fragment according to <8>, wherein the gene is preferably a gene encoding an enzyme involved in synthesis of an organic acid.

<10> A transformant comprising the expression vector according to any one of <4> to <7> or the DNA fragment according to <8> or <9>.

<11> The transformant according to <10>, wherein the transformant is preferably a filamentous fungus.

<12> The transformant according to <11>, wherein the filamentous fungus is preferably a filamentous fungus of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* or

*Trichoderma*, more preferably a fungus of *Rhizopus*, further preferably *Rhizopus oryzae*, or *Rhizopus delemar*, and still preferably *Rhizopus delemar*.

<13> A method of producing a substance of interest, comprising:
culturing a transformant comprising an expression, vector or a DNA fragment comprising a gene encoding a substance of interest or an enzyme involved in synthesis of the substance and the promoter according to any one of <1> to <3> linked upstream of the gene; and collecting the substance of interest from a culture obtained in the culturing.

<14> The method of producing according to <13>, wherein the substance of interest is an organic acid and the gene is a gene encoding an enzyme involved in synthesis of an organic acid.

<15> The method of producing according to <14>, wherein the organic acid is fumaric acid, lactic acid, succinic acid, malic acid or α-ketoglutaric acid.

EXAMPLES

While the present invention is described below in further detail based on Examples, the present invention is not limited by them.

Example 1: Identification of a Promoter (1) Genome Extraction

Spores of *Rhizopus delemar* JCM (Japan Collection of Microorganisms/Riken) 5557 strain (hereinafter, referred to as 5557 strain) were inoculated into PDA medium and then cultured at 30° C. for 5 days. After culturing, fungus bodies were placed in a 3 mL tube together with metal cones for 3 mL (Yasui Kikai Corporation) and immediately frozen for 10 minutes or more in liquid nitrogen. Then, the fungus bodies were crushed for 10 seconds at 1,700 rpm using Multi-beads shocker (Yasui Kikai Corporation). 400 μL of TB Buffer (pH 8.0) (NIPPON GENE CO., LTD.) was added to the vessel after crushing and admixed with inverting, and 250 μL of the mixture was transferred to a 1.5 mL tube. Genome extraction from the fungus body solution was conducted according to the protocol using "Dr. GenTLE™ (from Yeast) High Recovery (Yeast Solution)" (TAKARA BIO INC.). 1 μL of RNaseA (Roche Diagnostics K.K.) was added to 50 μL of the obtained genome solution and the resulting mixture was reacted at 37° C. for 1 hour. After the reaction, an equal amount of phenol chloroform was added to the mixture and the resulting mixture was admixed by tapping, and then centrifuged at 4° C. at 14,500 rpm for 5 minutes, and the supernatant was transferred to a new 1.5 mL tube. The phenol chloroform process was repeated again and then ethanol precipitation was conducted to obtain a purified genome solution of 5557 strain.

(2) Genome Sequencing

Genome sequencing was conducted using MiSeq Sequencer (Illumina, Inc.). Namely, the purified genome solution of 5557 strain obtained in the (1) was processed using Nextera XT DNA Sample Preparation Kit (Illumina, Inc.) and the obtained sample was subjected to MiSeq. The operation was conducted according to the recommended protocol. After the analysis in MiSeq, the outputted sequence information was analyzed using CLC Genomics Workbench (CLC bio). The genome sequence of *Rhizopus delemar* RA 99-880 strain obtained from Broad Institute (www.broadinstitute.org/scientific-community/science/projects/fungal-genome-initiative/mucorales-genomes) was used as a reference sequence.

(3) Total RNA Extraction 6 g-wet weight of fungus bodies of 5557 strain were inoculated into 40 mL of liquid medium (0.1 g/L $(NH_4)_2SO_4$, 0.6 g/L $KH_2PO_4$, 0.25 g/L $MgSO_4.7H_2O$, 0.09 g/L $ZnSO_4.7H_2O$, 50 g/L calcium carbonate and 100 g/L glucose) and cultured at 35° C. at 170 rpm for 8 hours. The fungus bodies were filtered and collected from the culture solution, and washed twice with 100 mL of 0.85% saline. After washing, excess water was removed by suction filtration and then 0.3 g of the fungus bodies was weighed and collected, and placed in a 3 mL tube together with a metal cone for a 3 mL tube (Yasui Kikai Corporation), and the tube was immediately placed in liquid nitrogen to freeze the fungus bodies. The obtained frozen fungus bodies were crushed for 10 seconds at 1,700 rpm using Multi-beads shocker (Yasui Kikai Corporation). 500 μL of RLT buffer was added to the fungus bodies after crushing and the resulting mixture was admixed with inverting, and 450 μL of the mixture was subjected to RNeasy Plant Mini Kit (Qiagen) and total RNA extraction was conducted. 1 μL of DNaseI (TAKARA BIO INC.) and 5 μL of 10×DNaseI buffer (USB Corporation) were added to 40 μL of the obtained RNA solution, and the mixture was filled up to 50 μL with RNase free water and then reacted at 37° C. for 30 minutes or more to remove the remaining DNA in the solution. 1 μL of DNaseI was further added to the solution and the resulting mixture was reacted at 37° C. for 30 minutes and then phenol/chloroform extraction was conducted, and then ethanol precipitation was conducted. The precipitate was dissolved in 50 μL of sterile water and the concentration and purity of the RNA solution were measured using Qubit (Life Technologies). The RNA solution was diluted as appropriate and the assay of the extracted RNA was conducted using Agilent 2100 Bioanalyzer (Agilent Technologies) and RNA 6000 Pico Kit (Agilent Technologies).

(4) Transcriptome Analysis

Transcriptome analysis was conducted using MiSeq Sequencer (Illumina, Inc.). Samples were prepared from the total RNA solution extracted in the (3) using TruSeq RNA sample Prep v2 LS Kit (Illumina, Inc.). At that time, the samples were prepared so that the fragment length of the RNA is 150 nucleotides. The prepared samples were subjected to MiSeq to analyze the transcript amount. Contigs were formed to analyze the outputted data using CLC Genomics Workbench (CLC bio) and the transcript amount was calculated with RPKM value (Reads Per Kilobase of exon per Million mapped fragments). The RPKM value is a value obtained by standardizing the map read number mapped against each RNA sequence with the total read number and the length of RNA sequences of each sample, and can be calculated by the following formula.

$$RPKM=C/NL$$

C: the total number of reads mapped against one RNA sequence
N: the total read number mapped against the total RNA sequence (million)
L: the sequence length of contig (kbase)

(5) Identification of High Expression Promoter Sequence

The 5557 strain genome was annotated by conducting BLAST analysis using the gene sequence of *R. delemar* RA 99-880 strain obtained from Broad Institute and the gene sequence obtained from NCBI (www.ncbi.nlm.nih.gov/) as a database and using the obtained RNA sequence as a query. The genome regions with high transcript amounts were identified based on the obtained annotation information and the result of the transcript amount analysis of the (4).

The result proved that the 5557 strain genome regions annotated as an adh1 gene, a cipC gene and an nmt1 gene have significantly high transcript amounts. The RPKM values of the genes and the RPKM value of the gene encoding PDCA (pdcA) which has the promoter with the highest promoter activity among known promoters for reference are shown in Table 1. The upstream 1,000 bp, 729 bp, and 1,000 bp regions (SEQ ID NOs: 1 to 3, respectively) of adh1, cipC and nmt1 of the 5557 strain genome were obtained as the promoter sequences of the genes.

TABLE 1

| Gene | RPKM value |
| --- | --- |
| adh1 | 10633.56 |
| cipC | 10462.90 |
| nmt1 | 14265.42 |
| pdcA (reference) | 3766.45 |

Example 2: Production of a Transformant (1) Production of a Tryptophane Auxotroph The tryptophane auxotrophs used as a host strain of gene transfer were selected and obtained from the 5557 strains mutated by ion beam irradiation. The ion beam irradiation was conducted in an ion irradiation facility of Takasaki Ion Accelerators for Advanced Research Application (TIARA) of Japan Atomic Energy Agency. 100 to 1,250 Gray was irradiated at energy of 220 MeV by accelerating $^{12}C^{5+}$ using an AVF cyclotron. Spores were collected from the irradiated fungus bodies, and from them, the *Rhizopus delemar* 02T6 strain having 1 nucleotide deletion mutation in the trpC gene region and exhibiting tryptophane auxotrophy was obtained.

(2) Production of a Plasmid Vector (i) Introduction of the trpC Gene Region into pUC18

DNA fragments of a trpC gene were synthesized by PCR using primer oJK162 (SEQ ID NO: 4) and oJK163 (SEQ ID NO: 5) and the genomic DNA of the 5557 strain as a template. Next, the DNA fragments were amplified by PCR using primer oJK164 (SEQ ID NO: 6) and oJK165 (SEQ ID NO: 7) and the plasmid pUC18 as a template. The 2 types of fragments were linked using In-Fusion HD Cloning Kit (Clontech Laboratories, Inc.) to construct a plasmid pUC18-trpC.

(ii) Cloning of an adh1 Promoter and Terminator

The promoter fragment and the terminator fragment of adh1 were amplified by PCR using primer oJK202 (SEQ ID NO: 8) and oJK204 (SEQ ID NO: 9), as well as oJK205 (SEQ ID NO: 10) and oJK216 (SEQ ID NO: 11), respectively, and the genomic DNA of the 5557 strain as a template. Next, the DNA fragments were amplified by PCR using primer oJK210 (SEQ ID NO: 12) and oJK211 (SEQ ID NO: 13) and the plasmid pUC18-trpC obtained in (i) as a template. The 3 types of fragments were linked according to the same procedure as (i) to construct a plasmid pUC18-trpC-Padh-Tadh. The adh1 promoter and terminator are placed in order downstream of the trpC gene region in the obtained plasmid. Further, the Not I restriction enzyme recognition sequence is placed downstream of the adh1 terminator.

(iii) Cloning of β Glucuronidase Gene (Hereinafter, GUS)

The DNA fragment of a β glucuronidase (hereinafter, GUS) gene was amplified by PCR using primer oUT1 (SEQ ID NO: 14) and oUT2 (SEQ ID NO: 15) and pBI121 (TAKARA BIO INC.) as a template. Next, the DNA fragment was amplified using primer oJK268-1 (SEQ ID NO: 16) and oJK269-4 (SEQ ID NO: 17) and the plasmid pUC18-trpC-Padh-Tadh obtained in (ii) as a template. The 2 types of fragments were linked according to the same procedure as (i) to construct a plasmid vector pUC18-trpC-Padh-GUS-Tadh. A GUS gene is inserted between the adh1 promoter and terminator in the obtained plasmid.

(iv) Cloning of a cipC Promoter

The promoter fragment of cipC was amplified by PCR using primer oJK838 (SEQ ID NO: 18) and oJK839 (SEQ ID NO: 19) and the genomic DNA of the 5557 strain as a template. Next, the DNA fragment was amplified by PCR using primer oJK842 (SEQ ID NO: 20) and oJK843 (SEQ ID NO: 21) and the plasmid vector pUC18-trpC-Padh-GUS-Tadh produced in Example 2 (2) as a template. The 2 types of fragments were linked according to the same procedure as (i) to construct a plasmid vector pUC18-trpC-PcipC-GUS-Tadh. A GUS gene is inserted between the cipC promoter and the adh1 terminator in the pUC18-trpC-PcipC-GUS-Tadh.

The PCR primers used in the production of the plasmid vector pUC18-trpC-Padh-GUS-Tadh and pUC18-trpC-PcipC-GUS-Tadh are shown in Table 2.

TABLE 2

| Primer | Sequence (5'→3') | SEQ ID NO: |
| --- | --- | --- |
| oJK162 | cgagctcgaattatttaaatgaacagcaagttaataatctagaggg | 4 |
| oJK163 | tatgaccatgattacgatgagaggcaaaatgaagcgtac | 5 |
| oJK164 | atttaaataattcgagctcggtacccgggg | 6 |
| oJK165 | cgtaatcatggtcatagctg | 7 |
| oJK202 | tagagggaaaagagagaattgaaatagg | 8 |
| oJK204 | ttttgttatttaattgtattaattgataatg | 9 |
| oJK205 | aattaaataacaaaatcattttaattacgcattttc | 10 |
| oJK216 | catgattacgcggccgcgccattataatgcactagtg | 11 |
| oJK210 | ctcttttccctctaatgagaggcaaaatgaagcgtac | 12 |

TABLE 2-continued

| Primer | Sequence (5'→3') | SEQ ID NO: |
|---|---|---|
| oJK211 | atttaaatgtaatcatggtcatagctgtttc | 13 |
| oUT1 | aattaaataacaaaaatgttacgtcctgtagaaacccca | 14 |
| oUT2 | gcgtaattaaaatgatcattgtttgcctccctgctgcgg | 15 |
| oJK268-1 | ttttgttatttaattgtattaattgataatg | 16 |
| oJK269-4 | tcatttaattacgcattttcatttactaatttgttacattttgataacg | 17 |
| oJK838 | cattttgcctctcatggttactgaaactggtgtag | 18 |
| oJK839 | ctacaggacgtaacatggttagagtatgaagaaaaaaaaaaacg | 19 |
| oJK842 | atgttacgtcctgtagaaaccccaac | 20 |
| oJK843 | atgagaggcaaaatgaagcgtac | 21 |

(3) Gene Transfer to a Host Strain

The plasmid vector pUC18-trpC-Padh-GUS-Tadh and pUC18-trpC-PcipC-GUS-Tadh produced in the (2) were each treated with a Not Z restriction enzyme. 10 μL of the obtained DNA solutions (1 μg/μL) were added to 100 μL of a gold particle solution (60 mg/mL) and the resulting mixture was mixed, and then 40 μL of 0.1 M spermidine was added to the mixture and the resulting mixture was stirred well with vortex. Further, 100 μL of 2.5 M CaCl$_2$ was added to the mixture and the resulting mixture was stirred with vortex for 1 minute, and then centrifuged for 30 seconds at 6,000 rpm to remove the supernatant. 200 μL of 70% EtOH was added to the obtained precipitate and the resulting mixture was stirred with vortex for 30 seconds and then centrifuged at 6,000 rpm for 30 seconds to remove the supernatant. The obtained precipitate was resuspended in 100 μL of 100% EtOH.

Next, gene transfer to the spores of the 02T6 strain produced in the (1) with GDS-80 (Nepa Gene Co., Ltd.) was conducted using the DNA-gold particle solutions. The spores after the gene transfer were statically cultured for about 1 week under the condition of 30° C. on an inorganic agar medium (20 g/L glucose, 1 g/L ammonium sulfate, 0.6 g/L potassium dihydrogenphosphate, 0.25 g/L magnesium sulfate heptahydrate, 0.09 g/L zinc sulfate heptahydrate and 15 g/L agar). The grown fungus bodies were obtained as the Padh1-GUS strain into which the DNA sequence having the GUS gene linked downstream of the adh1 promoter is introduced and the PcipC-GUS strain into which the DNA sequence having the GUS gene linked downstream of the cipC promoter is introduced, respectively.

Example 3: Evaluation of Promoter Activity in the Padh1-GUS Strain and the PcipC-GUS Strain 2.5 g-wet weight of fungus bodies of the Padh1-GUS strain or the PcipC-GUS strain were inoculated into 40 mL of a liquid medium (0.1 g/L (NH$_4$)$_2$SO$_4$, 0.6 g/L KH$_2$PO$_4$, 0.25 g/L MgSO$_4$.7H$_2$O, 0.09 g/L ZnSO$_4$.7H$_2$O, 50 g/L calcium carbonate and 100 g/L glucose), and cultured at 35° C. at 170 rpm for 8 hours. The fungus bodies were obtained by filtering from the culture solution and washed twice with 100 mL of 0.85% saline. After washing, excess water was removed by suction filtration and 0.3 g of the fungus bodies was weighed and collected, and was placed in a tube with metal cones, and the tube was immediately placed in liquid nitrogen to freeze the fungus bodies for 10 minutes or more. The tube containing the frozen fungus bodies was processed with Multi-beads shocker at 1,700 rpm for 10 seconds to crush the fungus bodies. 1 mL of an extraction buffer (50 mM NaPi (pH 7.2), 10 mM EDTA, 0.1% Triton-X-100, 0.1% N-lauroyl sarcosine Na and 1 mM DTT) was added to the samples after crushing to suspend them, and 900 μL of the obtained suspension was transferred to a 1.5 mL tube and centrifuged at 4° C. at 1,500 rpm for 10 minutes. 500 μL of the supernatant was transferred to a new 1.5 mL tube and centrifuged again at 4° C. at 1,500 rpm for 10 minutes. 100 μL of the obtained supernatant was used as a crude enzyme solution. The protein amount of the obtained crude enzyme solution was measured using Quick Start™ Bradford Protein Assay (Bio-Rad Laboratories, Inc.).

A β glucuronidase (GUS) degrades 4-methylumbelliferone D-glucuronide and produces 4-methylumbelliferone. The GUS enzymatic activity in the crude enzyme solution was quantified based on the produced amount of 4-methylumbelliferone. 10 μL of the crude enzyme solution was added to 90 μL of a buffer for GUS activity measurement (50 mM NaPi (pH 7.2), 10 mM EDTA, 0.1% Triton-X-100, 0.1% N-lauroyl sarcosine Na, 1 mM DTT and 1.16 mM 4-methylumbelliferone D-glucuronide) and incubated at 37° C. for 60 minutes, and then 900 μL of 0.2 M Na$_2$CO$_3$ was added to the mixture to stop the reaction. The absorbance of the reaction solution was measured with Infinite M1000 PRO (Tecan Trading AG, Switzerland) (excitation: 365 nm, measurement: 455 nm). The absorbance of the solution to which 4-methylumbelliferone was added in a given dilution series instead of 4-methylumbelliferone D-glucuronide in the buffer was measured under the same condition to make a standard curve. 4-methylumbelliferone amount in the reaction solution was calculated based on the standard curve. From the calculated amount, the amount of 4-methylumbelliferone (nmol) produced in the crude enzyme solution per 1 minute of the reaction was further calculated, and the amount was used as 1 Unit. GUS activity values (Unit/mg protein) were calculated by dividing the 1 Unit by the protein amount in the crude enzyme solution. The measurement was conducted in n=3. The result is shown in Table 3. It was confirmed that GUS, a heterologous protein, was expressed in the Padh1-GUS strain and the PcipC-GUS strain into which the adh1 promoter-GUS gene constructs were introduced.

TABLE 3

| Strain | GUS activity value (Unit/mg-protein; mean ± SD, n = 3) |
| --- | --- |
| Padh1-GUS | 2474.87 ± 231.16 |
| PcipC-GUS | 2522.73 ± 356.28 |
| 02T6 (negative control) | N.D. |

Example 4: Contrast with a Known Promoter (1) Production of PpdcA-GUS Strain

The fragment of a pdcA promoter, a known promoter, was amplified by PCR using the primer oJK855 (SEQ ID NO: 22) and oJK856 (SEQ ID NO: 23) described in Table 4 and the genomic DNA of the 5557 strain as a template, and then the pUC18-trpC-PpdcA-GUS-Tadh was constructed according to the same procedure as Example 2 (2) (iv). A GUS gene is inserted between the pdcA promoter and the adh1 terminator in the pUC18-trpC-PpdcA-GUS-Tadh. The Not I restriction enzyme recognition sequence is placed downstream of the adh1 terminator.

Next, the PpdcA-GUS strain into which the DNA sequence having the GUS gene linked downstream of the pdcA promoter is introduced was obtained according to the same method as Example 2 (3).

TABLE 4

| Primer | Sequence (5'→3') | SEQ ID NO: |
| --- | --- | --- |
| oJK855 | cattttgcctctcatgcagacttcaacagttggc | 22 |
| oJK856 | tacaggacgtaacatgtttttaaatttgttttgtagag | 23 |

(2) Comparison of the Promoter Activity

The GUS activity value of the PpdcA-GUS strain was measured according to the same procedure as Example 3. The activity value of the obtained PpdcA-GUS strain and the activity values of the Padh1-GUS strain and the PcipC-GUS strain measured in Example 3 are shown in Table 5. The Padh1-GUS strain and the PcipC-GUS strain have significantly higher GUS activities compared to the PpdcA-GUS strain, and this result shows that the activities of the adh1 promoter and the cipC promoter are significantly higher than that of the pdcA promoter having the highest promoter activity among known promoters. Further, the transcript amounts (RPKM values, Table 1) measured in Example 1 were correlated with the GUS activity values shown in Table 5 and thus it was suggested that the nmt1 promoter exhibiting the highest maximal RPKM value in Table 1 has even the higher promoter activity than those of adh1 and cipC promoters. Therefore, the adh1 promoter, the cipC promoter and the nmt1 promoter are the promoters which can express any gene even higher.

TABLE 5

| Strain | GUS activity value (Unit/mg-protein; mean ± SD, n = 3) |
| --- | --- |
| PpdcA-GUS | 1067.11 ± 230.39 |
| Padh1-GUS | 2474.87 ± 231.16 |
| PcipC-GUS | 2522.73 ± 356.28 |

Example 5: Activity of a *Rhizopus oryzae*-Derived adh1 Promoter (1) Production of a PRoadh1-GUS Strain A *Rhizopus delemar* PRoadh1-GUS strain, a transformant into which a *Rhizopus oryzae*-derived adh1 promoter is introduced, was produced.

The fragment (SEQ ID NO: 24) of the *Rhizopus oryzae*-derived adh1 (hereinafter, Roadh1) promoter were amplified by PCR using the primer oJK1165 (SEQ ID NO: 25) and oJK1166 (SEQ ID NO: 26) described in Table 6 and the genomic DNA of the *Rhisopus oryzae* NBRC5384 strain (hereinafter, 5384 strain) as a template, and then a plasmid vector pUC18-trpC-PRoadh1-GUS-Tadh was constructed according to the same procedure as Example 2 (2) (iv). A GUS gene is inserted between the Roadh1 promoter and the adh1 terminator in the pUC18-trpC-PRoadh1-GUS-Tadh. The Not I restriction enzyme recognition sequence is placed downstream of the adh1 terminator. Next, the obtained pUC18-trpC-PRoadh1-GUS-Tadh was introduced into the *Rhizopus delemar* 02T6 strain according to the same method as Example 2 (3) to obtain a transformant PRoadh1-GUS strain into which the DNA sequence having the GUS gene linked downstream of the Roadh1 promoter is introduced.

TABLE 6

| Primer | Sequence (5'→3') | SEQ ID NO: |
| --- | --- | --- |
| oJK1165 | cattttgcctctcatattattattagagggaaaagaaaaaaagagaattgg | 25 |
| oJK1166 | tacaggacgtaacattttgttatttatttgtattaattgataatg | 26 |

(2) Confirmation of the Roadh1 Promoter Activity in the PRoadh1-GUS Strain 6.0 g-wet weight of the fungus bodies of the PRoadh1-GUS strain were cultured, and a crude enzyme solution was prepared from the culture, and the protein amount of the crude enzyme solution was measured and then the GUS activity of the crude enzyme solution was quantified according to the same procedure as Example 3. The result is shown in Table 7. It was confirmed that GUS, a heterologous protein, was expressed in the PRoadh1-GUS strain into which the Roadh1 promoter-GUS gene construct is introduced. This result shows that the *Rhizopus oryzae*-derived adh1 promoter had a promoter activity in the transformant.

TABLE 7

| Strain | GUS activity value (Unit/mg-protein; mean ± SD, n = 3) |
| --- | --- |
| PRoadh1-GUS | 375.05 ± 15.38 |
| 02T6 (negative control) | N.D. |

What is claimed is:

1. A promoter construct comprising
a promoter consisting of a DNA selected from the group consisting of the following (a) to (c); and a DNA sequence exogenous to the promoter operably linked to the promoter:
   (a) a DNA consisting of the nucleotide sequence of any one of SEQ ID NOs: 1 to 3;
   (b) a DNA consisting of a nucleotide sequence having at least 90% identity to the nucleotide sequence of any one of SEQ ID NOs: 1 to 3 and having promoter activity; and
   (c) a DNA consisting of a nucleotide sequence wherein one to ten nucleotides are deleted, substituted or added in the nucleotide sequence of any one of SEQ ID NOs: 1 to 3 and having promoter activity.

2. The promoter construct according to claim 1, wherein the promoter DNA is the DNA of part (b) and the DNA of part (b) is a DNA having 95% or more identity to the nucleotide sequence of any one of SEQ ID NOs: 1 to 3.

3. The promoter construct according to claim 1, wherein the promoter DNA is the DNA of part (b) and the DNA of part (b) is a DNA having 98% or more identity to the nucleotide sequence of any one of SEQ ID NOs: 1 to 3.

4. An expression vector comprising the promoter construct according to claim 1.

5. The expression vector according to claim 4, wherein the promoter is operatively linked upstream of a gene encoding a protein or nucleic acid of interest or encoding an enzyme involved in synthesis of a substance of interest.

6. The expression vector according to claim 5, wherein the substance of interest is an organic acid, and the gene is a gene encoding an enzyme involved in synthesis of the organic acid.

7. A DNA fragment comprising a gene encoding a protein or nucleic acid of interest or encoding an enzyme involved in the synthesis of a substance of interest, and a promoter consisting of a DNA selected from (a) to (c) below that is exogenous to and operatively linked upstream of the gene
   (a) a DNA consisting of the nucleotide sequence of any one of SEQ ID NOs: 1 to 3;
   (b) a DNA consisting of a nucleotide sequence having at least 90% identity to the nucleotide sequence of any one of SEQ ID NOs: 1 to 3 and having promoter activity; and
   (c) a DNA consisting of a nucleotide sequence wherein one to ten nucleotides are deleted, substituted or added in the nucleotide sequence of any one of SEQ ID NOs: 1 to 3 and having promoter activity.

8. The DNA fragment according to claim 7, wherein the substance of interest is an organic acid, and the gene is a gene encoding an enzyme involved in synthesis of the organic acid.

9. A transformed host cell comprising the expression vector according to claim 4.

10. The transformed host cell according to claim 9, wherein the transformed host cell is a filamentous fungus.

11. The transformed host cell according to claim 10, wherein the filamentous fungus is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* or *Trichoderma.*

12. The transformed host cell according to claim 11, wherein the filamentous fungus is *Rhizopus.*

13. A transformed host cell comprising the DNA fragment according to claim 7.

14. The transformed host cell according to claim 13, wherein the transformed host cell is a filamentous fungus.

15. The transformed host cell according to claim 14, wherein the filamentous fungus is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, or *Trichoderma*.

16. The transformed host cell according to claim 15, wherein the filamentous fungus is a *Rhizopus*.

17. A method of producing a substance of interest, comprising: culturing a transformed host cell that comprises an expression vector or a DNA fragment comprising a gene encoding a protein, nucleic acid or an enzyme involved in synthesis of a substance of interest; and a promoter consisting of a DNA selected from the group consisting of the following (a) to (c) operatively linked upstream of the gene:
   (a) a DNA consisting of the nucleotide sequence of any one of SEQ ID NOs: 1 to 3;
   (b) a DNA consisting of a nucleotide sequence having at least 90% identity to the nucleotide sequence of any one of SEQ ID NOs: 1 to 3 and having promoter activity; and
   (c) a DNA consisting of a nucleotide sequence wherein one to ten nucleotides are deleted, substituted or added in the nucleotide sequence of any one of SEQ ID NOs: 1 to 3 and having promoter activity; and collecting the substance of interest from a culture obtained in the culturing,
wherein the gene is exogenous to the promoter.

18. The method of producing according to claim 17, wherein the transformed host cell is a filamentous fungus.

19. The method of producing according to claim 17, wherein the substance of interest is an organic acid and the gene is a gene encoding an enzyme involved in synthesis of the organic acid.

20. The method of producing according to claim 18, wherein the substance of interest is an organic acid and the gene is a gene encoding an enzyme involved in synthesis of the organic acid.

21. A method of controlling expression of an gene that is exogenous to a promoter that is operatively placed downstream of the promoter, wherein the promoter consists of a DNA selected from the group consisting of the following (a) to (c):
   (a) a DNA consisting of the nucleotide sequence of any one of SEQ ID NOs: 1 to 3;
   (b) a DNA consisting of a nucleotide sequence having at least 90% identity to the nucleotide sequence of any one of SEQ ID NOs: 1 to 3 and having a promoter activity; and
   (c) a DNA consisting of a nucleotide sequence wherein one to ten nucleotides are deleted, substituted or added in the nucleotide sequence of any one of SEQ ID NOs: 1 to 3 and having a promoter activity.

* * * * *